United States Patent [19]

Willcock

[11] Patent Number: 4,484,821

[45] Date of Patent: Nov. 27, 1984

[54] METHOD AND APPARATUS FOR DETERMINING THE NO-FLOW TEMPERATURE OF A LIQUID

[75] Inventor: Richard R. Willcock, Chester, England

[73] Assignee: Shell Oil Company, Houston, Tex.

[21] Appl. No.: 587,867

[22] Filed: Mar. 13, 1984

Related U.S. Application Data

[63] Continuation of Ser. No. 390,453, Jun. 21, 1982, abandoned.

[30] Foreign Application Priority Data

Jul. 1, 1981 [GB] United Kingdom ................. 8120341

[51] Int. Cl.³ .................... G01N 25/12; G01N 11/00; G01K 13/00
[52] U.S. Cl. ........................................ 374/24; 73/64.1
[58] Field of Search ............................ 374/24, 16, 22; 73/64.1; 340/582, 580

[56] References Cited

U.S. PATENT DOCUMENTS

| | | | |
|---|---|---|---|
| 3,122,911 | 3/1964 | Conklin | 374/24 |
| 3,122,912 | 3/1964 | O'Neill et al. | 374/24 |
| 3,213,668 | 10/1965 | Thompson | 374/24 |
| 3,977,235 | 8/1976 | Topham | 73/54 |
| 4,023,397 | 5/1977 | Ouvrard | 374/24 |
| 4,292,837 | 10/1981 | Oakmon | 374/24 |

FOREIGN PATENT DOCUMENTS

| | | | |
|---|---|---|---|
| 1276943 | 6/1972 | United Kingdom | 374/24 |
| 1375862 | 11/1974 | United Kingdom | 73/54 UX |
| 171668 | 5/1965 | U.S.S.R. | 374/24 |
| 361397 | 12/1972 | U.S.S.R. | 374/24 |
| 446817 | 10/1974 | U.S.S.R. | 374/24 |
| 840721 | 6/1981 | U.S.S.R. | 374/24 |

*Primary Examiner*—Howard A. Birmiel
*Assistant Examiner*—Tom Noland

[57] ABSTRACT

A method of sensing the no-flow temperature of a liquid comprising the steps of varying the temperature of the liquid, sensing the temperature of the liquid, supplying pressure pulses to the liquid and sensing the resistance of the liquid to the flow of the pressure pulses as an indication of the ability of the liquid to flow.

8 Claims, 3 Drawing Figures

METHOD AND APPARATUS FOR DETERMINING THE NO-FLOW TEMPERATURE OF A LIQUID

This is a continuation of application Serial No. 390,453, filed June 21, 1982 and now abandoned.

BACKGROUND OF THE INVENTION

This invention relates to a method of and apparatus for determining the no-flow temperature of a liquid, such as domestic heating oil, plastic, paint, ice cream, margarine, oil, distillate fuel and aviation fuel. The determination of the no-flow temperature of such materials is important, because their production and handling is limited by their low temperature properties. It is evident that significant problems may arise, for example, if fuels such as aviation fuel or domestic fuel fail to flow through the handling system to a burner because of their limiting low temperature properties.

One of the critical specifications of liquids such as jet fuel, is the freeze point which is defined as the temperature at which wax crystals formed on cooling disappear when the temperature of an agitated fuel sample is allowed to rise. A major shortcoming of the freeze point specification is that it bears little relation to the fuel property that limits low temperature performance, viz., the ability of the fuel to flow from a fuel tank at low temperature. A prior art cold flow test consists of characterizing fuel by its hold-up factor, which is defined as the amount of fuel that is unable to flow from a first section of a tester to a second section and varies with the temperature of the fuel. The most important test parameter is the "zero percent hold-up temperature", which represents the lowest temperature to which the fuel can be subjected before total hold-up will occur, that is, the point at which none of the fuel can flow. It is this temperature that is likely to define the limit of a specification based on the low temperature flow properties of the fuel. The zero percent hold-up temperature cannot be determined directly by the prior art techniques. Rather, the usual procedure consists of constructing a graph of the temperature dependence of the hold-up factor over a range of readily determined values, which are typically between 10–90% hold-up, and extrapolating the plot to zero percent hold-up to obtain the zero percent hold-up temperature by this method, several points are necessary to construct the hold-up temperature profile, particularly in the region of low hold-up factors. Obviously, this is a time-consuming exercise.

Therefore, it is an object of the present invention to provide a method of and an apparatus for determining the no-flow temperature of liquids.

SUMMARY OF THE INVENTION

In accordance with the present invention there is provided a method of sensing the no-flow temperature of a liquid comprising the steps of varying the temperature of the liquid, sensing the temperature of the liquid, supplying pressure pulses to the liquid and sensing the resistance of the liquid to the flow of the pressure pulses as an indication of the ability of the liquid to flow.

In addition, the present invention provides an apparatus for sensing the no-flow temperature of a liquid comprising means for varying the temperature of the liquid, means for sensing the temperature of the liquid, means for supplying pressure pulses to the liquid and means for sensing the resistance of the liquid to the flow of the pressure pulses as an indication of the ability of the liquid to flow.

The present invention provides a rapid and straightforward method for characterizing the low temperature flow properties of liquids and, in particular, avaiation fuels on the basis of the no-flow temperature of such liquids. Other objectives, advantages and applications of the present invention will be made apparent by the following detailed description of the preferred embodiments of the present invention.

DETAILED DESCRIPTION OF THE PREFERRED EMBODIMENTS

Figure 1:
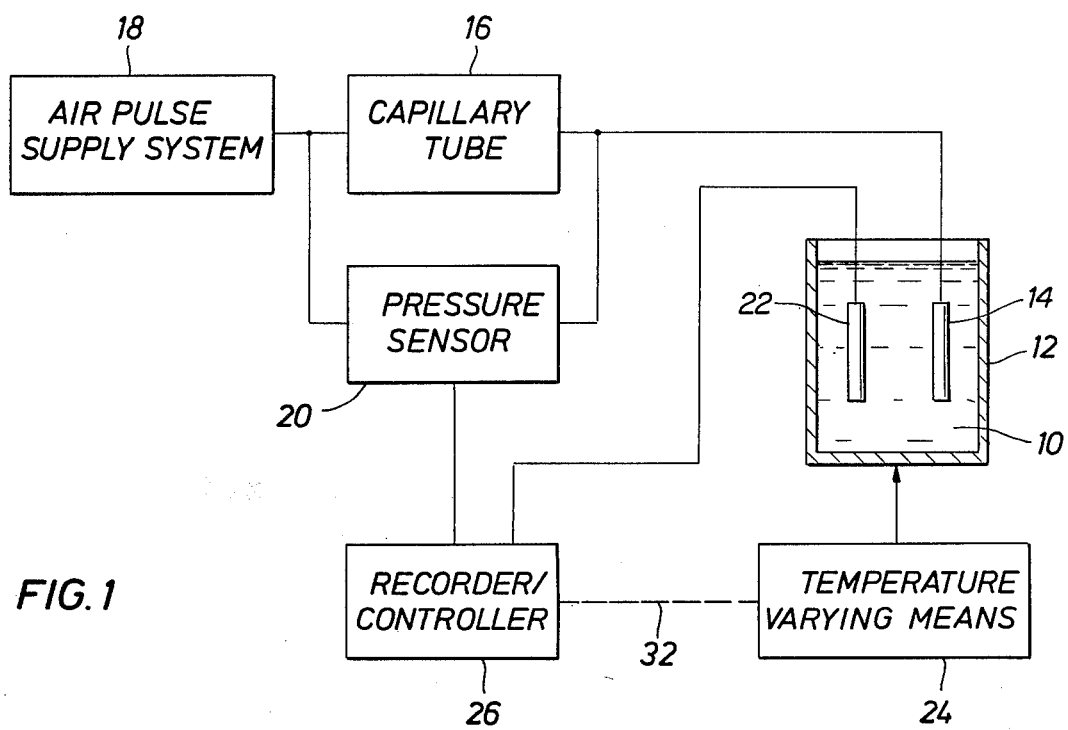
FIG. 1 is a schematic block diagram illustrating a liquid no-flow sensing system according to the present invention.

Referring to FIG. 1, a liquid sample 10, which is to be tested to determine its no-flow temperature, is contained within a sample holder 12. A probe 14 which is connected through a capillary tube 16 to an air pulse supply system 18 is positioned in liquid 10. Supply system 18 can comprise any means suitable for providing air pulses at suitable intervals through capillary 16 to probe 14. For example, supply system 18 can comprise an air supply, a drier, an air regulator, a manometer and a solenoid valve to provide dry pulsing air at about 9 millibars (7 millimeters mercury) pressure at one minute intervals. Capillary tube 16 can be, for example, a 0.4 millimeter glass capillary tube. Both ends of capillary tube 16 are connected to a suitable pressure monitor 20 which senses the differential pressure across capillary tube 16. The temperature of liquid 10 is sensed by temperature sensor 22 which is positioned in liquid 10 proximate to probe 14 and can consist of, for example, a thermocouple. The temperature of liquid 10 is varied by temperature varying means 24 which can be, for example, a cold bath or thermopile. The pressure sensed by pressure sensor 20 and the temperature sensed by temperature sensor 22 are provided to recorder/controller 26.

Figure 2:
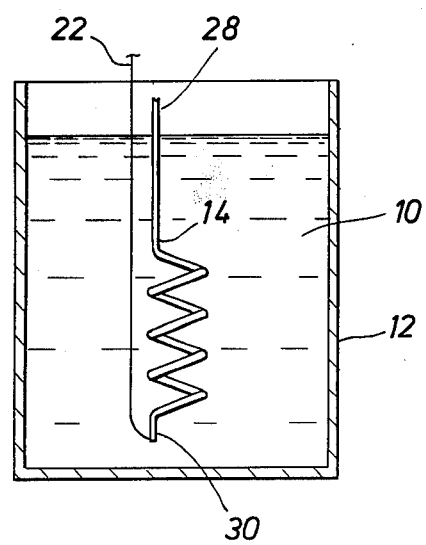
FIg. 2 is an enlarged view in elevation of the probe shown in FIG. 1.

An enlarged view of probe 14 is shown in FIG. 2. In this embodiment, probe 14 consists of a stainless steel tube having a bore of, for example, 0.6 millimeters. The air pulses from supply system 18 are provided to supply end 28 of probe 14 and are provided to liquid 10 at discharge end 30. In this embodiment, temperature sensor 22 is attached to discharge end 30 of probe 14.

Figure 3:
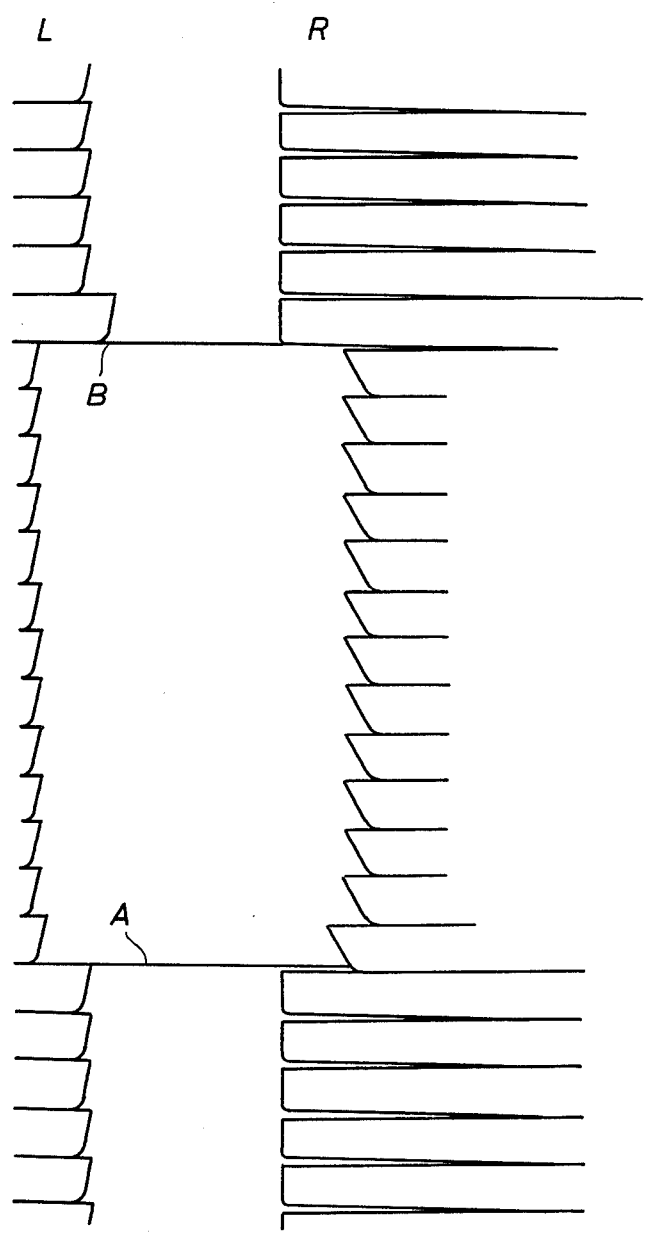
FIG. 3 illustrates a typical pressure trace obtained with the embodiment of the invention shown in FIG. 1.

FIG. 3 illustrates a typical pressure chart recorded by the present invention as disclosed in FIG. 1. Left-hand side, L, of the pressure trace, as viewed in FIG. 3, indicates the pressure downstream of capillary tube 16; whereas right-hand side, R, of the trace, as viewed in FIG. 3, indicates the pressure upstream of capillary tube 16. When air flow ceases due to, for example, wax formation on the tip of probe 14, the magnitude of the pressure signals changes as is indicated at point A. The inability of the air pulses to flow through liquid 10 is a direct indication of the loss of sample fluidity. The temperature at which this point occurs is the no-flow temperature of the liquid. If the temperature of liquid 10 is increased again, the air pulses can flow again as is indicated at point B.

In one embodiment, the pressure sensed by pressure sensor 20 and the temperature sensed by temperature sensor 22 can be merely recorded by recorder/controller 26, as the temperature of liquid 10 is varied by temperature varying means 24. In an alternative embodiment, recorder/controller 26, which can be, for example, a microcomputer, monitors the output of pressure sensor 20 to determine the point at which air pulses cannot enter liquid 10 from probe 14. When recorder/controller 26 determines that the no-flow point has been reached, the output of temperature sensor 22 is recorded and/or indicated by recorder/controller 26. In still another embodiment, temperature varying means 24 can be controlled by recorder/controller 26, as indicated by dotted line 32.

The operation of the system of the present invention, as disclosed in FIG. 1, can be described as follows. Supply system 18 provides dry air pulses through capillary tube 16 to probe 14. The differential pressure across capillary tube 16 is sensed by pressure sensor 20 and this pressure is provided to recorder/controller 26. The temperature of liquid 10 is sensed by temperature sensor 22, and this temperature is provided to recorder/controller 26. Temperature varying means 24 continues to decrease the temperature of liquid 10 at least to the temperature at which pressure pulses can no longer flow from probe 14 into liquid 10. Recorder/controller 26 determines the point at which the air pulses no longer flow from probe 14 and records the temperature sensed by temperature sensing means 22 at that time. If desired, temperature varying means 24 can be utilized to increase the temperature of liquid 10 while the pressure differential across capillary tube 16 and the temperature of liquid 10 are again monitored in order to determine the temperature at which the pressure pulses can again flow into liquid 10. Alternatively, recorder/controller 26 can be employed to merely record the pressure sensed by pressure sensor 20 and the temperature sensed by temperature sensor 22 to provide an indication of the no-flow temperature.

It is is to be understood that variations and modifications of the present invention can be made without departing from the scope of the invention. It is also to be understood that the scope of the invention is not to be interpreted as limited to the specific embodiments disclosed herein, but only in accordance with the appended claims when read in light of the foregoing disclosure.

What is claimed is:

1. A method of sensing the no-flow temperature of a liquid, said method comprising the steps of: supplying pressure pulses to said liquid through a supply line that includes a serially connected capillary tube and a serially connected probe which is positioned in said liquid; varying the temperature of said liquid by decreasing the temperature of said liquid at least to the temperature at which said pressure pulses cannot flow into said liquid and increasing the temperature of said liquid at least to the temperature at which said pressure pulses can flow into said liquid; sensing the temperature of said liquid proximate to the location at which said pressure pulses are supplied to said liquid; and sensing the resistance of said liquid to the flow of said pressure pulses as an indication of the ability of said liquid to flow by sensing the differential pressure across said capillary tube.

2. A method as recited in claim 1, wherein said resistance sensing step includes sensing when said pressure pulses cannot flow into said liquid and said temperature sensing step includes indicating the temperature at which said pressure pulses cannot flow into said liquid.

3. A method as recited in claim 1, further including the step of recording the temperatures sensed in said temperature sensing step and the resistances sensed in said resistance sensing step.

4. An apparatus for sensing the no-flow temperature of a liquid, said apparatus comprising: means for varying the temperature of said liquid; means for sensing the temperature of said liquid; means for supplying pressure pulses to said liquid including a probe adapted for insertion in said liquid, a capillary tube and a supply line serially connecting said probe and said capillary tube; and means for sensing the resistance of said liquid to the flow of said pressure pulses as an indication of the ability of said liquid to flow including means for measuring the differential pressure across said capillary tube.

5. Apparatus as recited in claim 4, wherein said resistance sensing means comprises means for sensing when said pressure pulses cannot flow into said liquid and said temperature sensing means comprises means for indicating the temperature at which said pressure pulses cannot flow into said liquid.

6. An apparatus as recited in claim 4, wherein said temperature sensing means is positioned to sense the temperature of said liquid proximate to said probe.

7. An apparatus as recited in claim 6, wherein said temperature sensing means comprises a thermocouple.

8. An apparatus as recited in claim 4, further comprising means for recording the sensed temperature and the sensed resistance.

* * * * *